United States Patent [19]
Ghyczy

[11] Patent Number: 6,126,941
[45] Date of Patent: Oct. 3, 2000

[54] PHOSPHOLIPIDIC COMPOSITION, METHOD FOR THE PRODUCTION OF SUCH A COMPOSITION AND ITS USE

[75] Inventor: Miklos Ghyczy, Cologne, Germany

[73] Assignee: Rhone-Poulenc Rorer GmbH & Co., Cologne, Germany

[21] Appl. No.: 08/955,233

[22] Filed: Oct. 21, 1997

[30] Foreign Application Priority Data

Nov. 6, 1996 [DE] Germany ............... 196 45 657

[51] Int. Cl.⁷ .................................... A61K 35/78
[52] U.S. Cl. ............... 424/195.1; 514/724; 514/783
[58] Field of Search ............. 424/195.1; 514/724, 514/783

[56] References Cited

U.S. PATENT DOCUMENTS

| | | | |
|---|---|---|---|
| 4,493,847 | 1/1985 | Mizushima et al. | 424/317 |
| 4,684,633 | 8/1987 | Imagawa et al. | 514/78 |
| 5,021,570 | 6/1991 | Ida et al. | 514/681 |
| 5,175,012 | 12/1992 | Shin et al. | 426/542 |

FOREIGN PATENT DOCUMENTS

| | | |
|---|---|---|
| 0372669 | 12/1988 | European Pat. Off. . |
| 301278 | 2/1989 | European Pat. Off. . |
| 53-062847 | 6/1978 | Japan . |
| 54-155205 | 12/1979 | Japan . |
| 63-283735 | 11/1988 | Japan . |
| 04039397 | 10/1992 | Japan . |
| 05058878 | 3/1993 | Japan . |
| 09009911 | 1/1997 | Japan . |
| 2063237 | 7/1996 | Russian Federation . |
| 8500746 | 2/1985 | WIPO . |
| 9520945 | 8/1995 | WIPO . |

*Primary Examiner*—Howard C. Lee
*Attorney, Agent, or Firm*—Proskauer Rose LLP

[57] ABSTRACT

A phospholipidic composition provides resistance against rancidity and the development of undesirable odors. The composition includes at least one phospholipid and a stabilizer. The stabilizer is ground parts and/or an extract of a grain. The composition is prepared by simple and reliable methods of production.

41 Claims, No Drawings ically described stabilizer varies between 9:1 and 1:4, preferably between 6:1 and 1:2. If a relatively solid, especially durable granulate or powder of the inventive composition is desired, then the weight ratio of the at least one phospholipid and the already described stabilizer lies preferably between 1:1 and 1:4, while for softer granulates or powder of the inventive composition the weight ratio of the at least one phospholipid and the already described stabilizer varies between 9:1 and 1:1. In other words, by variation of the amount of the already mentioned stabilizer, a desired solidity of the granulized or pulverized inventive composition, or with liquid compositions, a desired viscosity, can be reproducibly adjusted.

PHOSPHOLIPIDIC COMPOSITION, METHOD FOR THE PRODUCTION OF SUCH A COMPOSITION AND ITS USE

BACKGROUND OF THE INVENTION

The present invention relates to a phospholipidic composition, a method for the production of such a composition as well as the use of the phospholipidic composition.

Phospholipidic compositions have been known for a long time and are used in various ways in the field of food, in food for animals, in the cosmetic field as well as in the pharmaceutical field. A problem has existed however, that such phospholipidic compositions, which depending on the concentration of phospholipides and the respective application, are liquid, semisolid, as especially gel-like, creamy, paste-like, or solid, and when exposed to air and/or when stored, very easily generate an inherent smell, especially an undesirable rancid smell.

To suppress this undesired change of odor of phospholipidic compositions, it is known, to provide the phospholipidic compositions with a stabilizer, wherein such stabilizers are built-up on the basis of vitamin C, vitamin E and/or their derivatives. Furthermore, for example according to DE 41 41 842 A1, phospholipidic compositions can also be protected against an undesired oxidation by using N-acyl-phosphatidylethanolamine.

Furthermore DE 40 21 082 A1 suggests that urea, monosaccharides or mixtures of urea with monosaccharides are suitable for use in the stabilization of phospholipidic compositions.

The object of the present invention is to provide a phospholipidic composition of the above mentioned type, which does not experience any significant change in odor when stored for a longer period of time, even when exposed to air.

SUMMARY OF THE INVENTION

This object is realized according to the invention by a phospholipidic composition.

The inventive phospholipidic composition contains at least one phospholipid as well as a stabilizer, wherein the composition comprises ground parts and/or an extract of grain as the stabilizer along with the at least one phospholipid.

Surprisingly it was discovered that the inventive phospholipidic composition containing ground parts and/or an extract of grain as a stabilizer, provides excellent stability even when stored under exposure to air, so that an undesired change in odor does not occur with the phospholipidic composition stabilized in such a way, even after a longer period of storage of several months. This leads to the fact that the inventive phospholipidic composition does not have to be stored like the other known phospholipidic compositions, under inert gas, as for example nitrogen, and at reduced temperatures, especially temperatures around the freezing point. In the inventive phospholipidic composition, the stabilizer already described above also positively affects the consistency of the phospholipidic composition, i.e. for phospholipidic compositions, showing a high content of phosphatidylcholine, the originally known waxlike consistency, which generally occurs already after a few minutes following the production of such phospholipidic compositions, is not observed with the inventive composition. Rather, depending on its process of production, the inventive composition stays powdery or granulized, so that further processing and handling of the inventive composition is simplified considerably in comparison to the usual, waxlike phospholipidic compositions. Accordingly, by virtue of the inventive composition, reproducible resultant products regarding the concentration of the phospholipide can be produced as for example creams, gels, ointments, dispersions, semisolid or liquid mixtures of liposomes, as the granulized or pulverized inventive composition can be proportioned or measured much more simply and accurately.

Within liquid phospholipidic compositions, the already mentioned stabilizer causes these liquid phospholipidic compositions to stabilize excellently against chemical degradation, so that accordingly there are no changes of the chemical structure of the phospholipids contained therein. This again leads to the fact that such liquid phospholipidic compositions have a mainly constant viscosity even after a longer storage period, so that accordingly, these liquid phospholipidic compositions can be exactly and reproducibly dosed.

DETAILED DESCRIPTION OF THE INVENTION

A first embodiment of the inventive composition provides a composition that comprises as a stabilizer ground parts and/or an extract of the seed husks and/or of the aleurone layer of grain. Therefore this embodiment of the inventive composition contains such ground grain parts or grain extracts, which are also normally referred to as ground bran parts and/or as bran extracts.

Preferably the inventive phospholipidic composition contains such ground bran parts and/or such bran extracts as a stabilizer, which are gained from grinding of the seed husks and/or from the aleurone layer and/or gained by extraction, preferably extraction with water or a watery system, from the seed husks and/or from the aleurone layer of wheat, oats, corn, rice, rye, barley and/or millet.

In the present application, by grain, all kinds of grass are meant, which are cultivated because of their edible fruit.

With regard to the weight ratio of the at least one phospholipid to the ground parts of the grain or to the ground parts of the seed husks and/or of the aleurone layer of grain in the inventive composition, it can be stated that this weight ratio is orientated on one hand at the desired stabilization and on the other hand at the desired solidity and consistency of the granulized or pulverized inventive phospholipidic composition. In the inventive composition, the weight ratio of the at least one phospholipid to the already described stabilizer normally varies between 9:1 and 1:4, preferably between 6:1 and 1:2. If a relatively solid, especially durable granulate or powder of the inventive composition is desired, then the weight ratio of the at least one phospholipid and the already described stabilizer lies preferably between 1:1 and 1:4, while for softer granulates or powder of the inventive composition the weight ratio of the at least one phospholipid and the already described stabilizer varies between 9:1 and 1:1. In other words, by variation of the amount of the already mentioned stabilizer, a desired solidity of the granulized or pulverized inventive composition, or with liquid compositions, a desired viscosity, can be reproducibly adjusted.

If, however, in the inventive composition, the already described grain extract or the extract of the seed husks and/or the aleurone layer of grain is used as a stabilizer, then with this embodiment of the inventive composition, the weight ratio of the at least one phospholipid to the already mentioned stabilizer varies between 9:0.02 and 1:0.08, preferably between 6:0.02 and 1:0.04. By varying the amount of the stabilizer, a desired storage stability can be adjusted also with this embodiment of the inventive composition, whereby with a desired extremely long storage period the amount of the stabilizers is heightened correspondingly to the quantities mentioned already.

With regard to the phospholipid comprised in the inventive composition, it is stated that in accordance therewith, such a phospholipid is chosen, which is especially a phospholipid or a mixture of phospholipids being isolated from plants, preferably soy beans.

It is especially suitable that the mixture of phospholipid contained in the inventive composition comprises at least 70% by weight of 1,2-diacylglycero-3-phosphatidylcholine.

With a further embodiment of the inventive composition, the mixture of phospholipid contained in the inventive composition comprises at least 76% by weight ±3% by weight of 1,2-diacylglycero-3-phosphatidylcholine and 3% by weight ±3% by weight of lyso-phosphatidylcholine.

Another, also suitable variation of the embodiment of the inventive composition provides that the mixture of phospholipides is a mixture of phospholipids with a high content of phosphatidylcholine and preferably comprises 93% by weight ±3% by weight of 1,2-diacylglycero-3-phosphatidylcholine and especially comprises at least 96% by weight of 1,2-diacylglycero-3-phosphatidylcholine, whereby as a further phospholipid especially 3% by weight ±3% by weight of lyso-phosphatidylcholine is contained additionally.

In addition to the phosphatidylcholine already described, the inventive composition may also contain preferably 1,2-diacylglycero-3-phosphoethanolamine, 1,2-diacylglycero-3-phosphoinositol, 1,2-diacylglycero-3-phosphoserine, 1,2-diacylglycero-3-phosphoglycerol and 1,2-diacylglycero-3-phosphate as further phospholipides, depending on the respective basic material and the isolation and purification method used.

A further preferred embodiment of the inventive composition comprises such a mixture of phospholipids, the acyl groups of the phospholipids contained in the mixture, and especially the acyl groups of the phosphatidylcholine provided in the mixture, consist of
61–73% by weight of linoleic acid residue,
10–14% by weight of palmitic acid residue,
8–12% by weight of oleic acid residue,
4–6% by weight of linolenic acid residue,
3–5% by weight of stearic acid residue, and/or
2% by weight of other fatty acid residues.

Such a mixture of phospholipids or phosphatidylcholines or the mixtures more precisely described in the following, especially show the described foregoing advantages of the inventive composition, as, based on their high concentration of unsaturated fatty acid residues (groups) even with the claim high purity factor, such phospholipides or phosphatidylcholines very quickly tend to assume the claimed waxlike consistency and, even when excluded from atmospheric oxygen, they quickly generate an inherent smell growing in intensity.

A further embodiment of the inventive composition comprises a mixture of phospholipids or a phosphatidylcholine, the 1-acyl groups of the phospholipides contained in the mixture or the 1-acyl groups of the phosphatidylcholine, consist of
45–61% by weight of linoleic acid residue,
19–26% by weight of palmitic acid residue,
8–12% by weight of oleic acid residue,
4–6% by weight of linolenic acid residue,
6–9% by weight of stearic acid residue, and/or
2% by weight of other fatty acid residues.

Also the inventive composition may comprise such a mixture of phospholipides or phosphatidylcholine, whose acyl groups in the 1-position contain the acyl groups (residues) already mentioned or other acyl groups. The acyl groups in the 2-position of such a mixture of phospholipids or phosphatidylcholine consist of
77–85% by weight of linoleic acid residue,
1–2% by weight of palmitic acid residue,
8–12% by weight of oleic acid residue,
4–6% by weight of linolenic acid residue,
0–1% by weight of stearic acid residue, and/or
2% by weight of other fatty acid residues.

A further embodiment of the inventive composition comprises as a mixture of phospholipids a liquid mixture of phospholipids, which is isolated of plants, preferably soy beans, whereby this liquid mixture of phospholipids contains at least 40% by weight of 1,2-diacylglycero-3-phosphatidycholine. Furthermore this liquid mixture of phospholipids contains the usual accompanying phospholipids as well as vegetable oils, especially sunflower oil, thistle oil, avocado oil, almond oil, soy oil, castor oil, peanut oil, wheat germ oil, carrot oil, hazelnut oil, palm kernel oil, sesame oil, olive oil, walnut oil, corn oil and others.

The present invention furthermore relates to a method for the production of the already described inventive composition.

This object is realized according to the invention by a method with the characteristics of the patent claim 16 or with the characteristics of the patent claim 23.

The inventive method for the production of the inventive phospholipidic composition already described provides that, the at least one phospholipide or the mixture of phospholipides is initially dissolved or dispersed in a solvent or mixture of solvents. Hereafter, this solution or this dispersion of the phospholipide or the mixture of phospholipids is added to a solution or dispersion of the stabilizer already described, in such a way that the mixture produced by formation of the inventive phospholipidic composition is then carefully dried, especially spray-dried or freeze-dried.

The inventive method provides the advantage that it can be performed in a relatively easy manner. This is based on the fact, that with the inventive method only two solutions or dispersions are mixed together, so that hereafter only this mixture is dried and by this the inventive composition becomes available in the respective granulized shape. It is also possible, of course, with the already described inventive method, to add the solution or dispersion of the stabilizer to the solution or dispersion of the phospholipid or mixture of phospholipides and, hereafter to carefully dry, especially spray-dry or freeze-dry this mixture.

Principally it is to be stated with regard to the selection of the solvent or mixture of solvents used with the inventive method, that the solvent or mixture of solvents for the phospholipid or the mixture of phospholipids, and the solvent or the mixture of solvents for the stabilizer, are adjusted to each other correspondingly in such a way, that these two solvents or mixtures of solvents are mixable between each other. As a solvent or as a mixture of solvents for the inventive method, preferably water and/or an alcohol or a mixture of alcohol, especially ethanol, 1-propanol and/or 2-propanol are used.

An especially suitable and preferred embodiment of the inventive method provides, that in accordance therewith an alcoholic solution of the phospholipids or the mixture of phospholipids is produced, especially an ethanolic solution of the phospholipid or mixture of phospholipids, and that thereafter this alcoholic solution is stirred or injected into a water dispersion or a water solution of the stabilizer. In the present description by water all those kinds of water systems are meant, as there are especially distilled water, deionized water, aqueous salt solutions or aqueous buffer systems, as for example phosphate buffers.

With regard to the concentration of the phospholipid or the mixture of phospholipids in the alcoholic solution it is to be stated that normally, with the inventive method, this alcoholic solution comprises between 70% by weight and 85% by weight of the phospholipid or of the mixture of phospholipides. Correspondingly, this alcoholic solution of phospholipids then comprises between 30% by weight and 15% by weight of the alcohol, especially ethanol.

Another embodiment of the inventive method provides that hereby an aqueous dispersion of the phospholipid is produced and that this aqueous dispersion of the phospholipid is then stirred or injected into the aqueous dispersion of the stabilizer. This variation of the inventive method provides the advantage, that alcohol can be avoided as a solvent, so that this variation of the inventive method is preferred in those cases where the respective manufacturer does not posses the corresponding equipment which allows the processing of inflammable solvents.

Preferably the aqueous dispersion already described comprises between 5% by weight and 20% by weight, especially between 8% by weight and 15% by weight, of the phospholipid or mixture of phospholipids.

If a stabilizer is used with the inventive method, which contains the ground parts of the seed husks and/or the aleurone layer of the grain and which, as already explained, can be generally titled as ground bran as well, then it is advisable, that the aqueous dispersion of the stabilizer contains between 10% by weight and 30% by weight, especially between 15% by weight and 20% by weight, of such a stabilizer.

If, with the already described variations of the inventive method, further substances shall be added, as there are especially the already mentioned oils, so that accordingly the composition produced in such a way comprises these further substances, then this can basically be achieved in three different ways.

The first possibility provides that hereby these further substances are added to the solution or dispersion of the phospholipid, while with the second possibility these further substances are added to the solution or the dispersion of the stabilizer. Also, as a third possibility, a separate solution or dispersion of these further substances can be produced, whereby this solution or dispersion is then added to the mixture of the solution of the phospholipids respectively the dispersion of the phospholipids and the solution of the stabilizer, respectively the dispersion of the stabilizer.

A further possibility for the production of the inventive composition provides that, hereby a liquid phospholipid or a liquid mixture of phospholipids is produced in such a way, that the phospholipid, respectively mixture of phospholipids is added to an oil, especially to the already described oils or to the mixtures of oils. Hereafter the phospholipid or mixture of phospholipids added to the oil, is mixed up with the stabilizer in a fluid bed, whereby the solid stabilizer, foregoingly described with the inventive composition, forms this fluid bed.

It is possible of course, to liquefy the phospholipids or mixture of phospholipid in a variation of the already described method in such a way, that it is not added to an oil but instead of that, the phospholipide or mixture of phospholipides itself is melted by heat by application of higher temperatures and the phospholipid or mixture of phospholipids melted by heat in such a way, is then mixed in a fluid bed, formed by the solid stabilizer, with the stabilizer.

Depending on the desired further use of the inventive composition, the composition, produced according to the already described methods, may be used as a granulate directly. In such case the granular size of the granulate varies between 0.01 mm and about 4 mm. If however, such a granulized embodiment of the inventive composition with regard to the granular size (particle size) is not desired, then a development of the inventive method provides, that the granulized inventive composition is ground thereafter to a powder by means of a suitable pulverizing equipment, whereby the particle size of this powder preferably lies between 0.018 mm and 0.04 mm, preferably between 0.15 mm and 0.07 mm.

With regard to the use of the inventive composition it is to be stated that the inventive composition is used especially for the production of cosmetics or pharmaceutical products. With the cosmetics the inventive composition may preferably be used for the production of skin care products, especially the usual creams, lotions, milks, basic components for ointments and/or basic components for creams.

In the pharmaceutical field, the main field of use of the inventive composition especially exists in the production of dietetics, whereby such dietetics contain then either only the already described phospholipids and the already mentioned stabilizers or the already described phospholipids, the thereby mentioned stabilizers and in addition also animal and especially vegetable oils, preferably sunflower oil, thistle oil, avocado oil, almond oil, soy oil, castor oil, peanut oil, wheat germ oil, carrot oil, hazelnut oil, palm kernel oil, sesame oil, olive oil, walnut oil and corn oil. These oils exist in the inventive composition with this embodiment especially in a concentration between 5% by weight and 30% by weight, preferably between 10% by weight and 20% by weight. Surprisingly it was discovered hereby, that the dietetics already mentioned possess a high storage stability and therefore do not generate an annoying inherent smell even when stored for months. Based on the fact that preferably such dietetics contain ground parts of the seed husks and/or the aleurone layer of the grain as a stabilizer, such dietary formulations (dietetics) contain a high percentage of roughage, so that a saturation results in feeding a few calories already. The phospholipids contained in such dietary preparations make the application much easier, as they prevent an unpleasant degradation of the preparations in the mouth and furthermore stimulate the process of swallowing. Also these phospholipids have a positive influence on the fat metabolism and protect the liver against today's environmental toxic substances.

Advantageous developments of the inventive composition as well as of the inventive methods are also contemplated within the scope of the invention The inventive composition and the inventive method are explained in the following by means of examples.

EXAMPLE 1

800 g of a phospholipid, which comprises at least 96% by weight of phosphatidylcholine as well as other accompanying phospholipids, were dissolved in 200 g of alcohol. The solution prepared in such a way was titled solution 1.

200 g of ground parts of the seed husks as well as the aleurone layer of the grain (bran) were dispersed in 800 g of water. The dispersion prepared in such a way was titled dispersion 1.

100 g of the solution 1 were mixed with 100 g of the dispersion 1, whereby the mixing process occurred by means of a fast running stirring device (1000 rpm) for a period of 5 minutes. Thereafter the liquid mixture prepared in such a way was subjected to the usual spray-drying.

Hereby a granulized composition I was produced, having a weight ratio of phospholipid to stabilizer of 4:1.

EXAMPLE 2

50 g of the solution 1 were mixed with 100 g of the dispersion, each prepared according to example 1, under the conditions mentioned therein.

The granulized composition II prepared in such a way, had a weight ratio of phospholipid to stabilizer of 2:1 after spray-drying.

EXAMPLE 3

50 g of the solution 1 were mixed with 400 g of the dispersion 1, prepared according to example 1, under the conditions mentioned therein. After the spray-drying the granulized composition III prepared in such a way, had a weight ratio of phospholipid to stabilizer of 1:2.

EXAMPLE 4

50 g of the solution 1 were mixed with 800 g of the dispersion 1, prepared according to the conditions mentioned in example 1. After the spray-drying the granulized composition IV had a weight ratio of phospholipid to stabilizer of 1:8.

EXAMPLE 5

50 g of the solution 1 were mixed with 100 g of the dispersion 1, prepared according to the conditions mentioned in example 1. 3 g of a sunflower oil was dripped into the mixture while stirring, whereby the so produced dispersion/emulsion was stirred for a further 10 minutes. The mixture prepared in such a way was spray-dried. Thereafter a granulized composition was generated, which in the following is titled composition V.

EXAMPLE 6

Comparative Example Using Tocopherol as a Stabilizer 80 g of the phospholipid described in example 1 were dissolved in 20 g of ethanol. 1 g of tocopherole was stirred into this alcoholic solution. Thereafter it was spray-dried. The so prepared composition VI had a smeary, waxlike consistency.

EXAMPLES 7–12

An aging test was performed on the already mentioned compositions I to VI to that effect, that the inherent smell of the compositions was judged by four people independent from each other, directly after the production as well as after a storage period of one week, of one month, of three months and of six months. For reasons of objectivity a freshly prepared sample of the corresponding composition was also judged in comparison in this sensory rating of the odor. The formation of the odor was rated according to a random classification, entailing the marks 1 to 4, whereby the mark 1 represents no change of odor and the mark 4 represents a strong, rancid impression of odor.

The results of this sensory rating of odor are described in the following table.

TABLE 1

| Example No. | composition No. | directly after the production | after one week | after one month | after three months | after six months |
|---|---|---|---|---|---|---|
| 7 | I | 1 | 1 | 1 | 2 | 2 |
| 8 | II | 1 | 1 | 1 | 1 | 1 |
| 9 | III | 1 | 1 | 1 | 1 | 1 |
| 10 | IV | 1 | 1 | 1 | 1 | 1 |
| 11 | V | 1 | 1 | 1 | 1 | 1 |
| 12 | VI (Comparative Example) | 1 | 1 | 2 | 3 | 3 |

I claim:

1. A phospholipidic composition, comprising:
   at least one phospholipid; and
   a chemical stabilizer, said stabilizer selected from the group consisting of ground parts of grain, an extract of grain, and mixtures thereof.

2. The composition according to claim 1, wherein said stabilizer is selected from the group consisting of ground parts of seed husks, an extract of the seed husks, ground parts of an aleurone layer of grain, an extract of the aleurone layer of grain, and mixtures thereof.

3. The composition according to claim 1, wherein the grain is selected from the group consisting of wheat, oats, corn, rice, rye, barley, millet and mixtures thereof.

4. The composition according to claim 2, wherein the grain is selected from the group consisting of wheat, oats, corn, rice, rye, barley, millet and mixtures thereof.

5. The composition according to claim 1, wherein:
   the stabilizer is comprised of said ground parts of the grain; and
   the weight ratio of the at least one phospholipid to the ground parts of the grain varies between about 9:1 and about 1:4 in the composition.

6. The composition according to claim 5, wherein the weight ratio of the at least one phospholipid to the ground parts of the grain varies between about 6:1 and about 1:2 in the composition.

7. The composition according to claim 1, wherein:
   the stabilizer is comprised of said extract of the grain; and
   the weight ratio of the at least one phospholipid to the extract of the grain varies between about 9:0.02 and about 1:0.08 in the composition.

8. The composition according to claim 7, wherein the weight ratio of the at least one phospholipid to the extract of the grain varies between about 6:0.02 and about 1:0.04 in the composition.

9. The composition according to claim 1, wherein the at least one phospholipid is isolated from plant matter.

10. The composition according to claim 9, wherein said plant matter is soy beans.

11. The composition according to claim 1, wherein the at least one phospholipid is a mixture of phospholipids.

12. The composition according to claim 9, wherein the mixture of phospholipids contains at least 70% by weight of 1,2-diacylglycero-3-phosphatidylcholine.

13. The composition according to claim 1, wherein the at least one phospholipid is a mixture of phospholipids comprising at least about
   76% by weight ±3% by weight of 1,2-diacylglycero-3-phosphatidylcholine, and
   3% by weight ±3% by weight of lyso-phosphatidylcholine.

14. The composition according to claim 1, wherein the at least one phospholipid is a mixture of phospholipids comprising at least about 93% by weight ±3% by weight of 1,2-diacylglycero-3-phosphatidylcholine, and 3% by weight ±3% by weight of lyso-phosphatidylcholine.

15. The composition according to claim 1, wherein said at least one phospholipid is a mixture of phospholipids selected from the group consisting of 1,2-diacylglycero-3-phosphoethanolamine, 1,2-diacylglycero-3-phosphoinositol, 1,2-diacylglycero-3-phosphoserine, 1,2-diacylglycero-3-phosphoglycerol, and 1,2-diacylglycero-3-phosphate.

16. The composition according to claim 1, wherein the at least one phospholipid is a mixture of phospholipids in which the acyl groups of the phospholipids included therein are composed of about 61–73% by weight of linoleic acid residue, 10–14% by weight of palmitic acid residue, 8–12% by weight of oleic acid residue, 4–6% by weight of linolenic acid residue, 3–5% by weight of stearic acid residue, and/or 2% by weight of other fatty acid residues.

17. The composition according to claim 1, wherein the at least one phospholipid is a mixture of phospholipids in which the 1-acyl groups of the phospholipids included therein are composed of about 45–61% by weight of linoleic acid residue, 19–26% by weight of palmitic acid residue, 8–12% by weight of oleic acid residue, 4–6% by weight of linolenic acid residue, 6–9% by weight of stearic acid residue, and/or 2% by weight of other fatty acid residues.

18. The composition according to claim 1, wherein the at least one phospholipid is a mixture of phospholipids in which the 2-acyl groups of the phospholipids included therein are composed of about 77–85% by weight of linoleic acid residue, 1–2% by weight of palmitic acid residue, 8–12% by weight of oleic acid residue, 4–6% by weight of linolenic acid residue, 0–1% by weight of stearic acid residue, and/or 2% by weight of other fatty acid residues.

19. The composition according to claim 1, wherein the at least one phospholipid is a liquid mixture of phospholipids isolated from soy beans, said mixture containing at least about 40% by weight of 1,2diacylglycero-3-phosphatidylcholine, the liquid mixture further comprising oils.

20. A method for the production of a phospholipidic composition, comprising:

adding at least one phospholipid to at least one solvent to create a phospholipid/solvent composition selected from the group consisting of a solution and a dispersion of the at least one phospholipid, adding the phospholipid/solvent composition to a chemical stabilizer composition containing at least another solvent, the composition selected from the group consisting of a solution and a dispersion, to create a phospholipid/stabilizer mixture, the stabilizer selected from the group consisting of ground parts of grain and an extract of grain; and drying the mixture.

21. The method according to claim 20, wherein said step of drying is spray-drying.

22. The method according to claim 20, wherein said step of drying is freeze-drying.

23. The method according to claim 20, wherein said at least one solvent and said at least another solvent are selected from the group consisting of water, an alcohol, and mixtures thereof.

24. The method according to claim 23, wherein said alcohol is selected from the group consisting of ethanol, 1-propanol, 2-propanol and mixtures thereof.

25. The method according to claim 20, wherein:

the phospholipid/solvent composition comprises an alcohol solution and the chemical stabilizer composition comprises water.

26. The method according to claim 25, wherein said step of adding the phospholipid/solvent composition to the chemical stabilizer composition is carried out by stirring.

27. The method according to claim 25, wherein said step of adding the phospholipid/solvent composition to the chemical stabilizer composition is carried out by injecting.

28. The method according to claim 25, wherein the alcohol solution comprises about 70% by weight to about 85% by weight of the at least one phospholipid and about 30% by weight to about 15% by weight of the alcohol.

29. The method according to claim 20, wherein:

the phospholipid/solvent composition is a water dispersion and the chemical stabilizer composition is another water dispersion.

30. The method according to claim 29, wherein said step of adding the phospholipid/solvent composition to the chemical stabilizer composition is carried out by stirring.

31. The method according to claim 29, wherein said step of adding the phospholipid/solvent composition to the chemical stabilizer composition is carried out by injecting.

32. The method according to claim 29, wherein the another water dispersion of the chemical stabilizer composition comprises about 5% by weight to about 20% by weight of the at least one phospholipid.

33. The method according to claim 32, wherein the another water dispersion of the chemical stabilizer composition comprises about 8% by weight to about 15% by weight of the at least one phospholipid.

34. The method according to claim 20, wherein:

the chemical stabilizer composition is a water dispersion comprising about 10% by weight to about 30% by weight of the stabilizer; and the stabilizer is ground parts of seed husks of the grain.

35. The method according to claim 20, wherein:

the chemical stabilizer composition is a water dispersion comprising about 10% by weight to about 30% by weight of the stabilizer; and the stabilizer is ground parts of an aleurone layer of the grain.

36. A method for the production of a phospholipidic composition, comprising:

adding at least one phospholipid to at least one oil to produce a liquid phospholipid-oil mixture; and mixing the phospholipid-oil mixture with a chemical stabilizer in a fluid bed, the stabilizer selected from the group consisting of ground parts of grain, an extract of grain, and mixtures thereof.

37. The method according to claim 36, wherein said stabilizer forms said fluid bed.

38. The method according to claim 20, further comprising:

grinding said mixture to a granular size between about 0.18 mm and about 0.04 mm.

39. The method according to claim 38, wherein said granular size is between about 0.15 mm and about 0.07 mm.

40. The composition according to claim 1, further comprising:

an agent selected from the group consisting of pharmaceutical, cosmetic agents, and mixtures thereof.

41. The method according to claim 20, further comprising:

adding an agent to said mixture, said agent selected from the group consisting of pharmaceutical, cosmetic agents, and mixtures thereof.

* * * * *